(12) United States Patent
Braun

(10) Patent No.: US 10,262,114 B2
(45) Date of Patent: Apr. 16, 2019

(54) METHOD, APPARATUS, AND COMPUTER PROGRAM PRODUCT FOR THE PACKAGING AND VERIFICATION OF MEDICATION INFORMATION

(71) Applicant: Aesynt Incorporated, Cranberry, PA (US)

(72) Inventor: Patrick J. Braun, Pittsburgh, PA (US)

(73) Assignee: Aesynt Incorporated, Cranberry, PA (US)

( * ) Notice: Subject to any disclaimer, the term of this patent is extended or adjusted under 35 U.S.C. 154(b) by 1065 days.

(21) Appl. No.: 14/013,566

(22) Filed: Aug. 29, 2013

(65) Prior Publication Data

US 2015/0066205 A1 Mar. 5, 2015

(51) Int. Cl.
| | | |
|---|---|---|
| *G06F 19/00* | (2018.01) | |
| *G16H 20/13* | (2018.01) | |
| *B65B 9/04* | (2006.01) | |
| *B65B 5/08* | (2006.01) | |
| *B65B 5/10* | (2006.01) | |
| *B65B 5/04* | (2006.01) | |
| *G07F 17/00* | (2006.01) | |

(52) U.S. Cl.
CPC .......... *G06F 19/3462* (2013.01); *G06F 19/00* (2013.01); *G16H 20/13* (2018.01); *B65B 5/04* (2013.01); *B65B 5/08* (2013.01); *B65B 5/103* (2013.01); *B65B 9/045* (2013.01); *G07F 17/0092* (2013.01)

(58) Field of Classification Search
CPC . B65B 9/045; G06F 19/3456; G06F 19/3462; G07F 17/0092; G07F 11/007; G16H 20/13

USPC .......... 53/410, 411, 476; 700/214, 215, 216, 700/240

See application file for complete search history.

(56) References Cited

U.S. PATENT DOCUMENTS

| | | | | |
|---|---|---|---|---|
| 3,628,694 A | * | 12/1971 | Nichols | B65B 11/50 221/265 |
| 3,759,011 A | * | 9/1973 | Akke | B29C 65/18 221/273 |
| 3,874,143 A | * | 4/1975 | Braber | B29C 51/422 53/133.8 |
| 4,012,888 A | * | 3/1977 | Nichols | B29C 51/18 53/131.3 |
| 4,672,553 A | * | 6/1987 | Goldberg | G06Q 10/08 198/349 |

(Continued)

*Primary Examiner* — Alexander Valvis
*Assistant Examiner* — Eduardo R Ferrero
(74) *Attorney, Agent, or Firm* — Alston & Bird LLP

(57) ABSTRACT

Example embodiments of the present invention may provide an efficient method of identifying unit doses of medication, and more specifically, to dispensing, identifying, packaging, and labeling unit doses of medication for distribution. In particular, methods may include receiving medication information, causing identifying information related to the medication information to be printed to a web of material, where the identifying information is printed at regular intervals, and preparing a medication unit dose to be dispensed to a container. Methods may further include verifying that the medication unit dose corresponds to the identifying information printed to the web of material, and joining the web of material to the container in response to the dispensed unit dose corresponding to the identifying information.

12 Claims, 7 Drawing Sheets

(56) References Cited

U.S. PATENT DOCUMENTS

| | | | | |
|---|---|---|---|---|
| 4,847,764 A * | 7/1989 | Halvorson | G06F 19/326 | 221/2 |
| 4,918,604 A * | 4/1990 | Baum | G09F 3/00 | 221/5 |
| 5,337,919 A * | 8/1994 | Spaulding | B65G 1/1373 | 221/127 |
| 5,348,061 A * | 9/1994 | Riley | G07F 17/0092 | 141/104 |
| 5,568,715 A | 10/1996 | Ebel et al. | | |
| 5,597,995 A * | 1/1997 | Williams | G06F 19/328 | 235/375 |
| 5,799,468 A * | 9/1998 | Eck | B65B 57/10 | 53/237 |
| 5,812,410 A * | 9/1998 | Lion | G07F 17/0092 | 221/9 |
| 5,839,257 A * | 11/1998 | Soderstrom | B65B 61/26 | 53/131.5 |
| 5,852,911 A * | 12/1998 | Yuyama | B65B 35/04 | 221/10 |
| 5,875,610 A * | 3/1999 | Yuyama | B29C 66/1122 | 53/168 |
| 5,884,456 A * | 3/1999 | Hansen | B65B 11/50 | 206/461 |
| 5,907,493 A * | 5/1999 | Boyer | G06F 19/3462 | 700/213 |
| 6,035,905 A * | 3/2000 | Griffin | B65B 1/36 | 141/100 |
| 6,109,000 A * | 8/2000 | Conti | B29C 65/18 | 53/282 |
| 6,155,485 A * | 12/2000 | Coughlin | G06F 19/326 | 235/383 |
| 6,208,911 B1 * | 3/2001 | Yamaoka | G07F 17/0092 | 221/2 |
| 6,219,587 B1 * | 4/2001 | Ahlin | G06F 19/3462 | 700/233 |
| 6,345,487 B1 * | 2/2002 | Luciano | B65B 35/08 | 53/147 |
| 6,449,927 B2 * | 9/2002 | Hebron | B65B 57/20 | 53/131.3 |
| 6,535,637 B1 * | 3/2003 | Wootton | B65B 57/00 | 221/102 |
| 6,681,935 B1 * | 1/2004 | Lewis | A61J 1/035 | 206/534 |
| 6,757,420 B2 * | 6/2004 | Krahn | G01N 21/9508 | 250/223 B |
| 6,771,369 B2 * | 8/2004 | Rzasa | G01J 3/02 | 250/339.07 |
| 6,820,399 B2 * | 11/2004 | Send | B65B 41/18 | 493/10 |
| 7,006,214 B2 * | 2/2006 | Rzasa | G01J 3/02 | 250/339.07 |
| 7,210,598 B2 * | 5/2007 | Gerold | G06F 19/3462 | 221/123 |
| 7,313,898 B1 * | 1/2008 | Eller | B65B 21/06 | 108/153.1 |
| 7,685,798 B2 | 3/2010 | Marzocchi | | |
| 7,930,064 B2 * | 4/2011 | Popovich, Jr. | G07F 17/0092 | 221/2 |
| 8,406,916 B2 | 3/2013 | Bentele et al. | | |
| 2004/0011806 A1 * | 1/2004 | Luciano | B65B 37/08 | 221/266 |
| 2004/0207842 A1 * | 10/2004 | Rzasa | G01J 3/02 | 356/328 |
| 2007/0220827 A1 * | 9/2007 | Conti | B65B 65/02 | 53/111 R |
| 2007/0262147 A1 * | 11/2007 | Braun | G06K 7/14 | 235/454 |
| 2008/0197042 A1 * | 8/2008 | Ullrich | B65B 9/045 | 206/531 |
| 2008/0312957 A1 * | 12/2008 | Luciano, Jr. | A61J 7/0069 | 705/2 |
| 2009/0260739 A1 * | 10/2009 | Fischer | B41J 3/407 | 156/64 |
| 2013/0218330 A1 * | 8/2013 | Chudy | G06F 19/3462 | 700/244 |

* cited by examiner

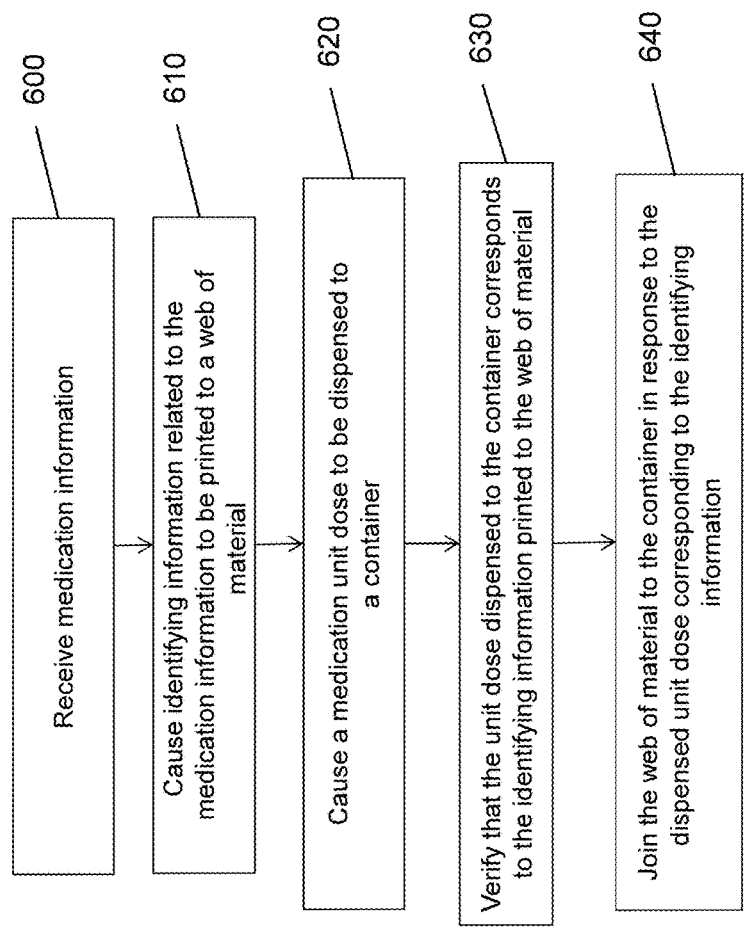

METHOD, APPARATUS, AND COMPUTER PROGRAM PRODUCT FOR THE PACKAGING AND VERIFICATION OF MEDICATION INFORMATION

FIELD OF THE INVENTION

Embodiments of the present invention relate to the identification of articles in an automated packaging system, and more particularly to providing a method, apparatus, and computer program product for ensuring accuracy and efficiency of the identification of medications dispensed in an automated pharmaceutical dispensing system.

BACKGROUND

Medications are an important part of an effective healthcare system, and it is important that medications are properly prescribed, distributed, and consumed. Advances in medication development have led to a proliferation of available medications for virtually any health condition. The vast number of medications available for patients can require pharmacies and hospitals to maintain very large inventories of medications with hundreds of types available at any given time. The large number of medications available may increase the likelihood of distributing the incorrect medication type or dosage to a patient. Manual verification of medicines, including the type and dosage, is generally required to minimize errors in distribution. However, as the number of available medications increases, the number of medications distributed to patients similarly increases. This increase has led to the automation of various steps of the medication distribution process.

Automated dispensing and packaging of medications is a process which must be executed with great accuracy to ensure patient safety and to minimize possible errors. Due to various phases of the distribution process, from the manufacturer to the wholesale distributor to the pharmacy to the patient, automation can be implemented in one or all of the distribution phases. However, upstream errors in packaging can be problematic if not caught before dispensing to a patient. Therefore, manual verification is still generally required to ensure accuracy of medication identification before it is distributed to a patient.

SUMMARY

Example embodiments of the present invention may provide an efficient method of verifying the contents of a container in a packaging machine, and more specifically, to identifying the contents of a container such as a blister, verifying the contents are correct, and allowing the packaging machine to complete the packaging operation in response to the container contents being correct. In particular, methods may include receiving medication information, causing identifying information related to the medication information to be printed to a web of material, where the identifying information is printed at regular intervals, and preparing a medication unit dose to be dispensed to a container. Methods may further include verifying that the medication unit dose corresponds to the identifying information printed to the web of material, and joining the web of material to the container in response to the dispensed unit dose corresponding to the identifying information. Verifying that the medication unit dose dispensed to the container corresponds to the identifying information may include capturing an image of the medication unit dose, and comparing identifying characteristics of the image of the dispensed unit dose to identifying characteristics of a medication unit dose corresponding to the identifying information. Capturing an image of the medication unit dose may include capturing an image of the medication unit dose dispensed to the container. Methods may include indexing the web of material with the container such that the identifying information printed to the web of material is aligned with the container. The medication information and corresponding identifying information may include a medication type and a medication dose. The medication information may further include at least one of expiration date, lot number, manufacturer, manufacture date, or location of manufacture. The identifying information may further include a barcode.

According to some embodiments of the present invention, receiving medication information may further include receiving medication information associated with a plurality of medication orders to be dispensed, each medication order including one or more unit doses of a single medication type and dose, and ordering the medication orders into a dispense order. Ordering the medications into a dispense order may include analyzing the plurality of medication orders to be dispensed, and ordering first and second medication orders including medications of similar appearance to include at least one medication order including a medication of a dissimilar appearance between them. Medications of similar appearance have at least one of color, shape, size, or indicia in common.

According to some embodiments of the present invention, an apparatus may be provided to package unit dose medications into containers, where the apparatus includes a printer configured to print identifying information about a medication to a web of material; a dispenser configured to dispense a medication to a unit dose container; and an image capture device configured to capture an image of at least one of the printed web or a dispensed medication unit dose. Apparatuses of example embodiments may further include a processor configured to verify that a dispensed medication unit dose matches identifying information of the printed web, and a joining station configured to join the printed web to a container containing the dispensed medication unit dose in response to the processor verifying that the dispensed medication unit dose matches the identifying information of the printed web. Identifying information about a medication may include medication type and medication dose. The joining station may include at least one of an ultrasonic welder or a heating element, each configured to seal the printed web of material to the container containing the dispensed medication unit dose.

Apparatuses according to embodiments of the present invention may further include an indexing station configured to align the printed identifying information with the container containing the dispensed medication unit dose. The apparatus of example embodiments may include a medication hopper configured to supply medication to the dispenser. A container forming station may be included where the container forming station forms containers from a second web of material.

According to some embodiments of the present invention, a computer program product may be provided including at least one non-transitory computer-readable storage medium having computer-executable program code instructions stored therein. The computer-executable program code instructions may include program code instructions for receiving an indication of a plurality of medication orders to be dispensed, where each medication order includes one or more unit doses of a single type of medication; program code instructions for ordering the plurality of medication orders to be dispensed into a dispensing order; and program code instructions for providing medication information related to a first medication order of the dispensing order to be dispensed. According to some embodiments, the computer program product may include program code instructions for causing identifying information related to the medication information to be printed to a web of material, where the identifying information is printed at regular intervals; program code instructions for causing a medication unit dose to be dispensed to a container; program code instructions for verifying that the unit dose dispensed to the container corresponds to the identifying information printed to the web of material; and program code instructions for joining the web of material to the container in response to the dispensed unit dose corresponding to the identifying information.

According to some embodiments, the program code instructions for ordering the plurality of medication orders to be dispensed into a dispensing order may include program code instructions for analyzing the medication type and dose of each of the plurality of medication orders, and program code instructions for generating a dispensing order in which medication orders including medications of similar appearance are separated by at least one medication order including a medication of a dissimilar appearance. Medications of similar appearance may have at least one of a color, shape, size or indicia in common. The program code instructions for verifying that the unit dose dispensed to the container corresponds to the medication information may include program code instructions for capturing an image of the dispensed unit dose, and program code instructions for comparing the image of the dispensed unit dose to a known image of a medication unit dose corresponding to the medication information. The medication information and corresponding identifying information may include a medication type and a medication dose.

BRIEF DESCRIPTION OF THE SEVERAL VIEWS OF THE DRAWINGS

Reference will now be made to the accompanying drawings, which are not necessarily drawn to scale, and wherein:

FIG. 7 is a flowchart of a method for verifying contents and packaging individual unit doses of medication.

DETAILED DESCRIPTION

Figure 1:
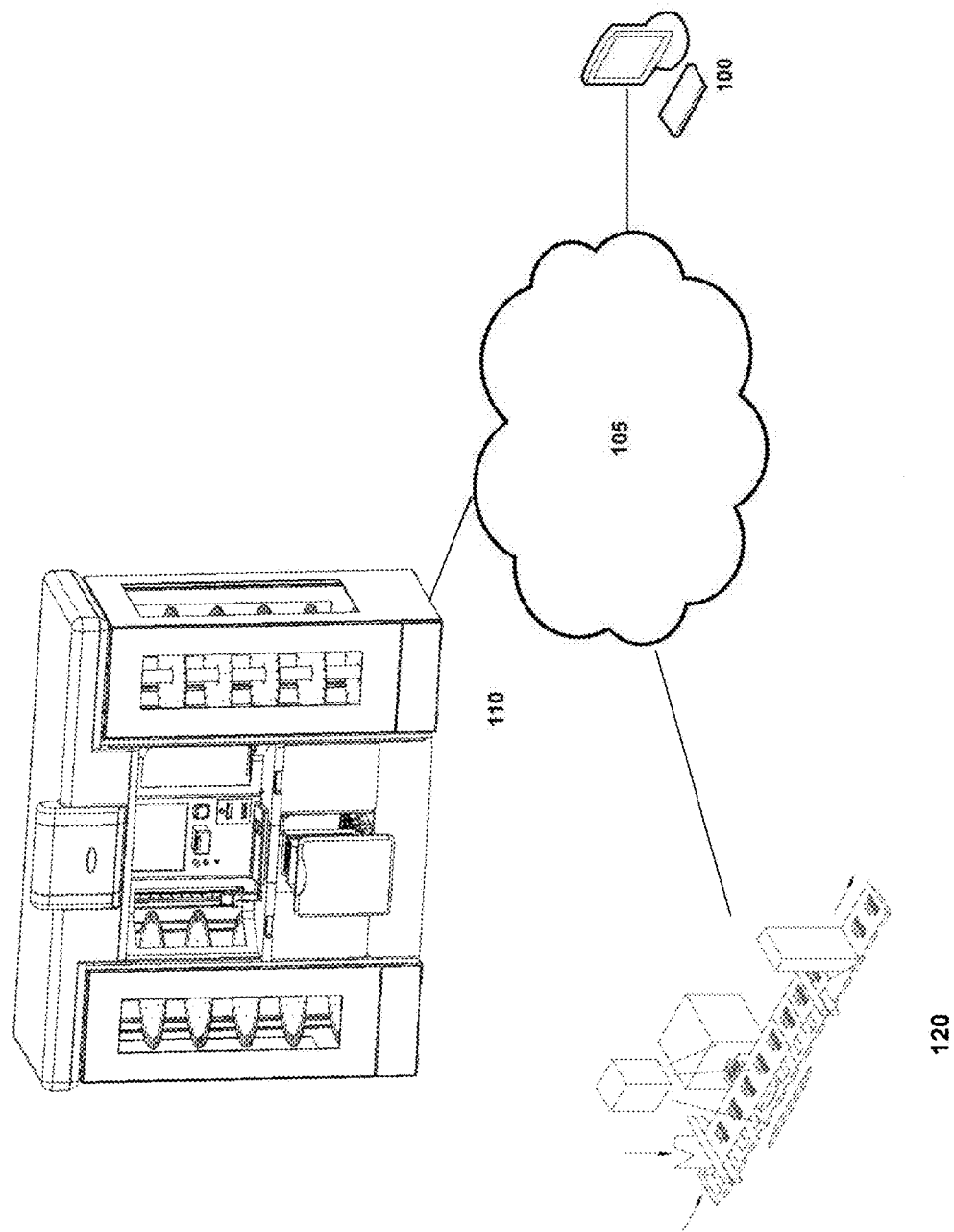
FIG. 1 illustrates a system that can be used in conjunction with various embodiments of the present invention.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. The terms top, bottom, side, up, down, upwards, downwards, vertical, horizontal, and the like as used below do not imply a required limitation in all embodiments of the present invention but rather are used herein to help describe relative direction or orientation in exemplary embodiments illustrated in the figures.

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of a system that can be used in conjunction with various embodiments of the present invention. As shown in FIG. 1, an example embodiment of the system may include an automated storage and/or dispensing system 110, one or more networks 105, and an automated packaging station 120. Embodiments may include various other devices which may be in communication with the one or more networks 105, such as an audit/approval station 100 which may be used for manual review and/or audit of an automated process performed by one or both of the automated storage and/or dispensing system 110 and the automated packaging station 120. Embodiments may further include other network entities from which data may be received from or transmitted to, as will be described further below. Each of the components of the system may be in electronic communication with, for example, one another over the same or different wireless or wired networks (e.g., network 105) including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

Figure 2:
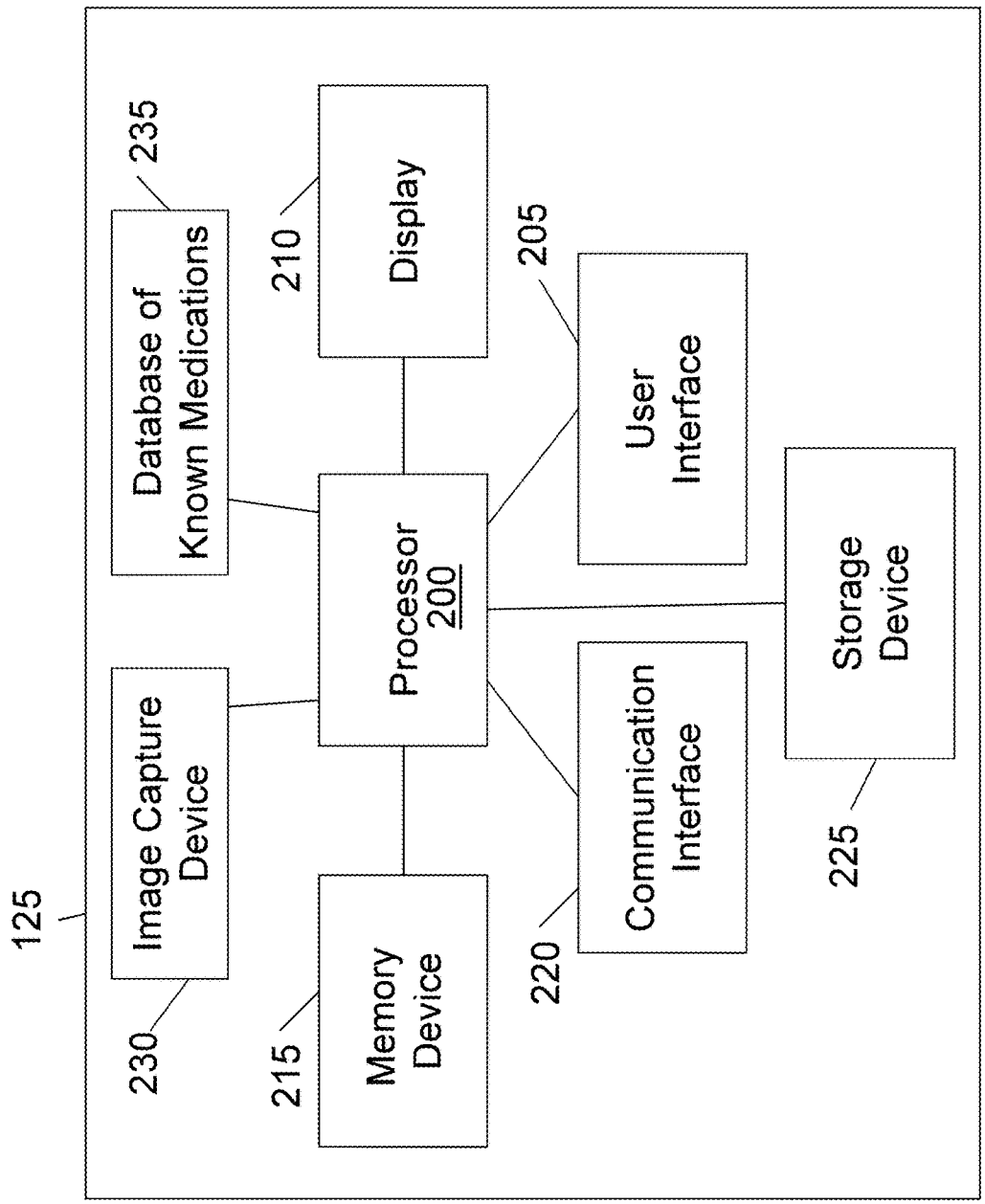
FIG. 2 illustrates a schematic diagram of an automated packaging station controller according to an example embodiment of the present invention.

Example embodiments of the automated packaging station 120 as described herein may include a controller configured to control or otherwise monitor and facilitate activities performed at the automated packaging station 120. FIG. 2 provides a schematic of an example embodiment of a controller 125 of an automated packaging station 120. In general, the term "controller" may refer to, for example, any computer, computing device, mobile phone, desktop, tablet, notebook or laptop, distributed system, server, blade, gateway, switch, processing device, or combination of processing devices adapted to perform the functions described herein. The automated packaging station controller 125 may include, be associated with, or be in communication with a variety of computing entities, such as pharmacy inventory management systems, a medication identification database, medication dispensing units, data storage/facilitation computing entities, or other devices that may interface with inventory management, dispensing, replenishing, etc. While example embodiments of automated storage and dispensing systems may be implemented in virtually any setting which may benefit from automated dispensing of articles, embodiments described herein will be described generally with respect to the field of healthcare in which medications may be dispensed for patients or caregivers. However, it is appreciated that embodiments of the present invention may apply to various other embodiments of automated storage and/or dispensing systems and devices.

As will be understood from FIG. 2, in one embodiment, the automated packaging station controller 125 may include a processor 200 that communicates with other elements of the automated packaging station controller 125 via a system interface or bus. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an example embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the automated packaging station controller 125 may be configured, among other things, to facilitate accurate verification of unit doses of medication as they are packaged. The automated packaging station controller 125 may also be used to facilitate printing of labels for unit dose medications, such as by printing medication identification information to a web of material that is used to seal a container including the identified medication. A user interface 205 may be configured for user input to initiate the automated packaging process or to confirm, advance, or otherwise interact with operations of the automated packaging process. The user interface 205 may include a keyboard, a pointing device, or other mechanism for a user to communicate with the processor 200 and interact with the automated packaging station controller 125.

Automated packaging station controllers according to example embodiments may further include a display 210 which may be configured to present information to a user pertaining to the automated packaging process and to communicate alerts or confirm success of various steps of the automated packaging process. The display 210 may also be configured to present information to a user pertaining to the status of the automated packaging station, information regarding inventory, or any information which may be useful to a user of the device. The display 210 may include a touch screen display which may partially or fully comprise the user interface 205. As noted above, example embodiments may include an automated packaging station that also incorporates the approval station. In such an embodiment, the user interface 205 and display 210 may be used for the approval of operations of the packaging process, auditing the automated packaging process, or reviewing rejected, unidentified unit dose medications as will be further detailed below.

The automated packaging station controller 125 may further include or be in communication with an image capture device 230. The image capture device may include a still camera, a video camera, and/or the like. The image capture device 230 of embodiments of the present invention may be used to capture images and/or video of a unit dose of medication once it is dispensed from a hopper containing a plurality of unit doses of medication and/or once a medication unit dose is manually dispensed to a package. Embodiments of the controller may further include or be in communication with a database of known medications 235 which includes identifying information regarding a plurality of medications. The database of known medications 235, as with any of the components of the automated packaging station controller 125, may be located remotely from the controller and may be accessed via a wired or wireless network. As such, the database of known medications may include identifying information for all of the medications configured to be processed by the automated packaging station.

The automated packaging station controller 125 may further include transitory and non-transitory memory device 215, which may include both random access memory (RAM) and read only memory (ROM). The ROM may be used to store a basic input/output system (BIOS) containing the basic routines that help to transfer information to the different elements within the automated packaging station controller 125.

In addition, in one embodiment, the automated packaging station controller 125 may include at least one storage device 225, such as a hard disk drive, a CD drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, an audit trail of medications identified and/or packaged, operations, errors, alerts, and manual identification of medications rejected by the identification system described below.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the automated packaging station controller 125 with the assistance of the processor 200 and operating system, although their functionality need not be modularized. In addition to the program modules, the automated packaging station controller 125 may store or be in communication with one or more databases.

Also located within the automated packaging station controller 125, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the automated storage device controller 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the automated packaging station controller's 125 components may be located remotely from other automated packaging station controller components. For example the storage device 225 may be located on a remote network entity. Furthermore, one or more of the components may be combined and additional components performing functions described herein may be included in the automated packaging station controller 125.

Figure 3:
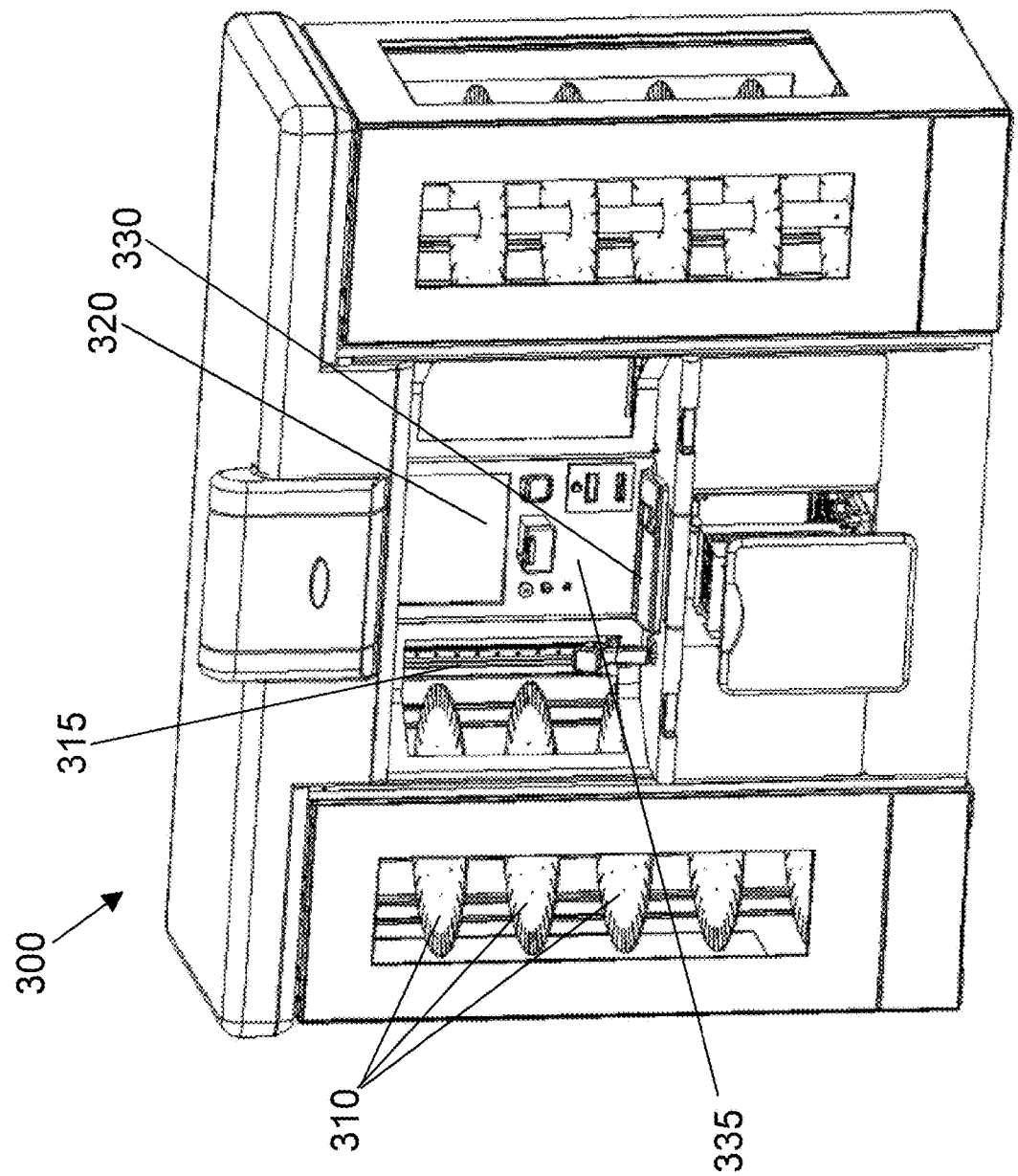
FIG. 3 illustrates an example embodiment of an automated storage and/or dispensing system which may benefit from example embodiments of the present invention.

In one embodiment, an automated storage and/or dispensing system may be used to hold/store/dispense various medications. Such dispensing systems may be used in a variety of environments, including retail pharmacies, central fill pharmacies, hospitals, etc. FIG. 3 illustrates an example embodiment of an automated storage and/or dispensing system 300 which may be configured to automatically dispense individual unit dose packages of medication in response to receiving a prescription order. Automated dispensing systems 300 which may benefit from example embodiments of the present invention may include a storage rack 310 which stores medication, such as unit dose packages. The storage rack 310 may be configured to hold a plurality of racks (not shown) configured to hold unit dose packages or trays of unit dose packages. The illustrated embodiment further includes a robotic system 315 within the automated storage and/or dispensing system 300 for retrieving the stored medications, where the robotic system 315 includes a mechanism for retrieving and moving the medications, and a dispensing area 335 where medications are dispensed for retrieval by a nurse, doctor, pharmacy technician, etc. In some embodiments, the automated storage and/or dispensing system may include an automated conveyor dispensing system for dispensing to patient-specific bins in an automated, sequential fashion to further enhance the automated dispensing operation. According to some embodiments of an automated dispensing system 300 which may benefit from embodiments of the present invention, the automated dispensing system 300 may include a user interface including a display 320 (e.g., a touch screen display) and/or a keyboard 330 or other user interface to allow a healthcare employee to request and retrieve medications.

Figure 4A:
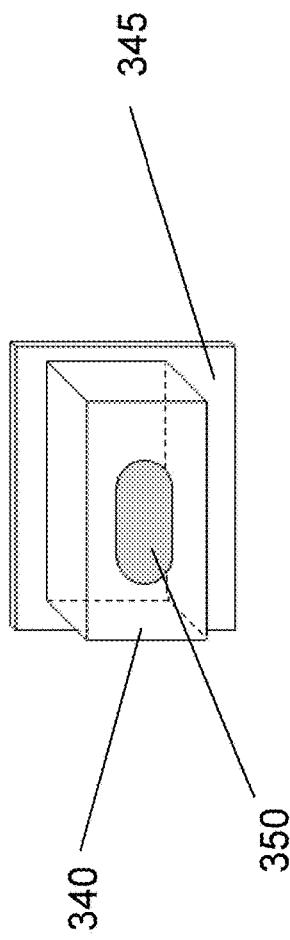
FIGS. 4A-4C illustrate a blister package including a medication unit dose disposed therein according to embodiments of the present invention.
Figure 4B:
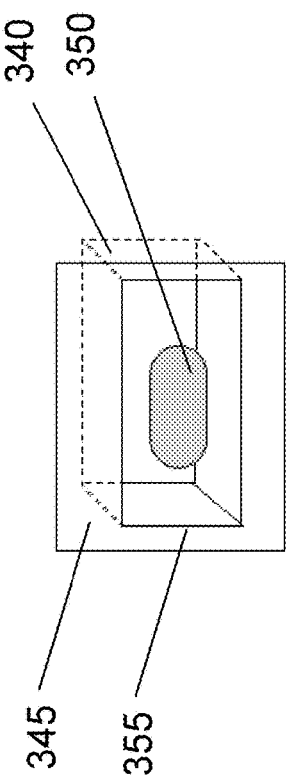
Figure 4C:
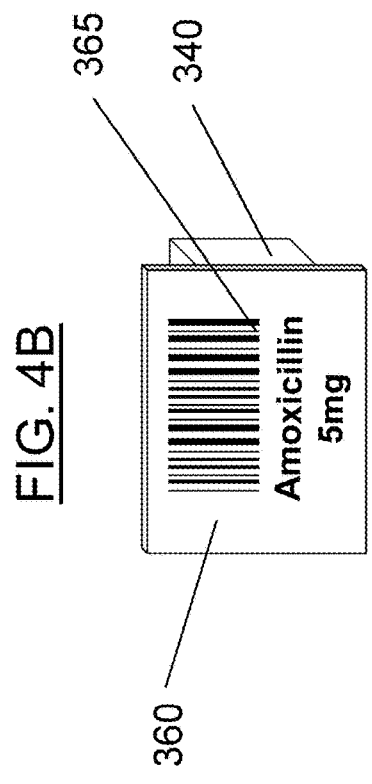

The unit doses of medication that are handled by some embodiments of automated storage and/or dispensing systems may require specific compatible packaging to be accurately and repeatably dispensed. Automated dispensing systems are generally implemented in environments where large quantities of medications are dispensed routinely, such as hospitals, central fill pharmacies serving several hospitals, healthcare facilities, and the like. As such, automated dispensing systems may dispense thousands to hundreds of thousands of individual unit doses annually. A common packaging container form may include a blister package, an example of which is illustrated in FIGS. 4A-4C. FIG. 4A depicts a front view of the blister package including a blister 340 which may be formed from a flat web of material by molding, stamping, or otherwise creating a cavity from the web of material. The portion of the web 345 which does not form part of the cavity of the blister 340 may create a flat surface or flange 345 surrounding the blister 340. FIG. 4B illustrates the back side of the blister package including an opening 355 through which a unit dose medication 350 may be inserted into the blister 340 cavity. A second material web 360 may be joined to the flange 345 surrounding the blister 340 to seal the unit dose medication 350 within the blister package. The second material web 360 may include medication identification information 365 printed thereon, as illustrated by the barcode and text shown in FIG. 4C. While FIGS. 4A-4C illustrate one example embodiment of a blister package container, other example embodiments of containers may be compatible with example embodiments of the present invention such that the invention should not be construed as limited to the specific packaging examples illustrated herein.

In order to track inventory, stock, and dispense medication accurately, particularly in automated storage and/or dispensing systems, medications must be packaged in the appropriate packaging and properly identified. The packaging, as illustrated in FIGS. 4A-C, may require specific identification 365 which may include an identifying barcode (one-dimension or two-dimension), a name, an encoded radio frequency identification (RFID) tag, or other identifying indicia. It is imperative that the medication contained within the packaging match the identifying information contained on the packaging. As automated dispensing systems and other devices, such as bed-side scanners used by nurses, may rely on the identification information on the packaging, the identifying information must be correct. Further, as a nurse, doctor, or patient may not know what the medication should look like, and because many medications resemble one another, it is important to properly identify the medication to avoid a patient receiving the incorrect medication (either type or dose).

Embodiments of the present invention provide a method, apparatus, and computer program product to properly package and identify packaged medication with appropriately printed labels such that the packaged medication can be properly handled throughout the dispensing process.

Figure 5:
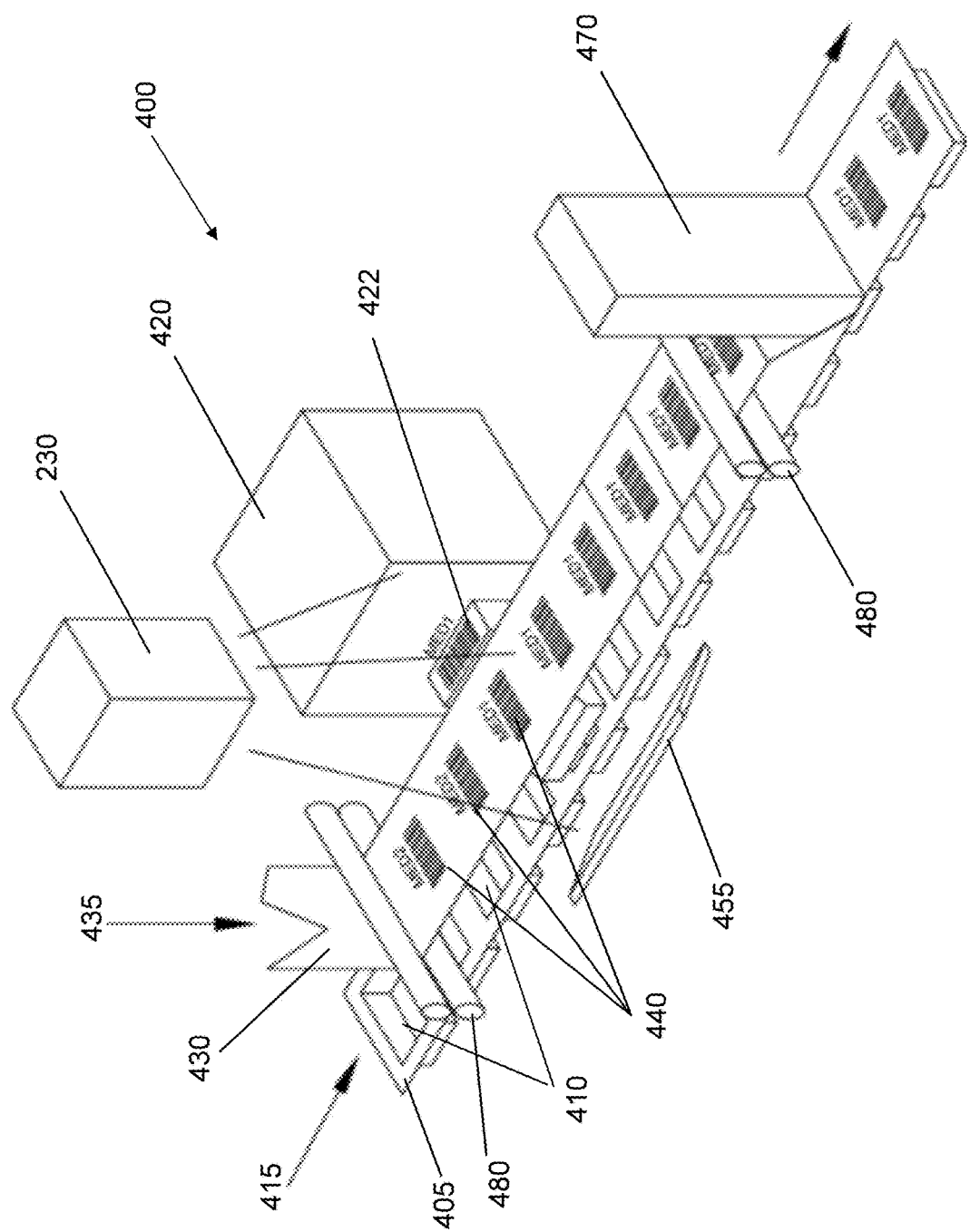
FIG. 5 is an illustration of an automated packaging station according to an example embodiment of the present invention.

FIG. 5 illustrates an example embodiment of an automated packaging station 400 in accordance with the present invention. The illustrated embodiment includes a packaging station which receives a first web of material 405 including container cavities 410 along the direction of arrow 415. The container cavities 410 are each configured to receive therein a unit dose medication. The unit dose medication may be loaded into the container cavities 410 manually, such as through an operator dispensing individual medications to a dispensing chute or in an automated manner as dispensed from a hopper 420. An example embodiment of a mechanism for dispensing is described further below. The hopper 420 may be configured with a unit dose singulator which ensures individual unit doses are dispensed one at a time, or the automated packaging station 400 may include a mechanism by which individual unit doses are individually dispensed from the hopper 420 to each container cavity 410. In some example embodiments, more than one unit dose may be dispensed to a container cavity 410. For example, the recommended dose for a particular medication, or a prescribed dose may require two pills of the medication to achieve the appropriate dosage.

Figure 6A:
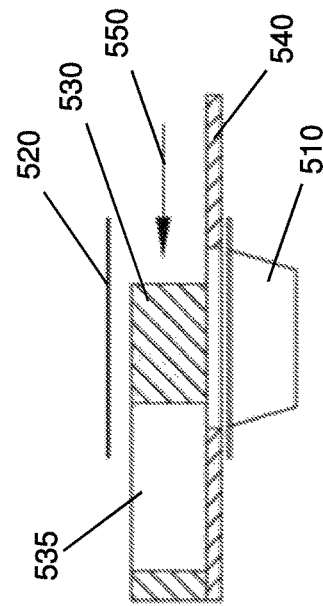
FIGS. 6A-6D illustrate a dispensing mechanism according to an example embodiment of the present invention.
Figure 6B:
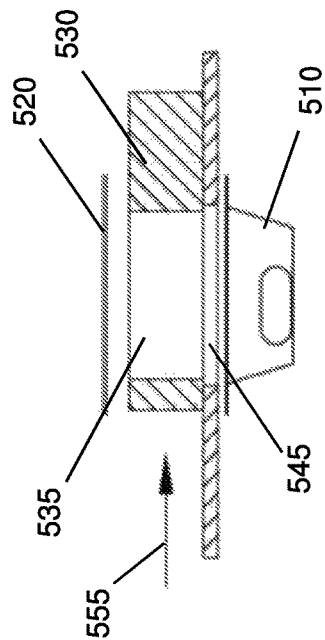
Figure 6C:
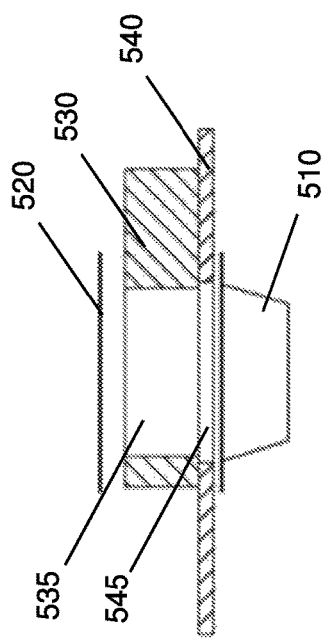
Figure 6D:
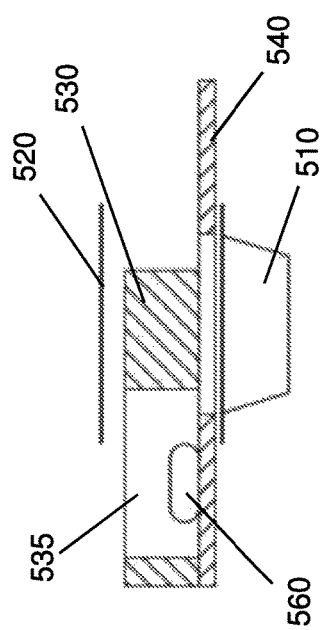

A second web of material 430 may be conveyed along a path illustrated by arrow 435 in order to join the second web of material 430 to the flange of the formed containers in order to seal the containers closed with the medication unit dose therein. FIGS. 6A-6D illustrate an example embodiment of a dispensing mechanism which may either be used with an automated dispensing hopper or loaded manually by an operator. The illustrated embodiment depicts a container 510 and second web of material 520 as viewed along their direction of motion (i.e., viewing along arrow 415 of FIG. 4). The illustrated embodiment includes a loading chute 530 and a barrier 540. The loading chute includes a cavity 535 and the barrier includes an opening 545 in communication with the cavity of the container 510. FIG. 6B illustrates the chute 530 advanced along arrow 550 to a position accessible to an operator or in communication with an automated hopper, depending upon the loading mechanism. In the loading position of FIG. 6B, a unit dose medication 560 is loaded (either manually or automatically) into the cavity 535 of the chute 530 as shown in FIG. 6C. The chute 530 may retract automatically along arrow 555 of FIG. 6D, or the chute 530 may require manual activation to retract. Optionally, the verification operation outlined below may be performed while the unit dose medication 560 is in the cavity 535 of the chute 530 rather than in the container cavity 510 as described in example embodiments below. In response to the chute 530 retracting to the position illustrated in FIG. 6D, the unit dose medication 560 may drop through the opening 545 into the cavity of the container 510. While the illustrated embodiment of FIGS. 6A-6D illustrate one mechanism by which a container may be loaded, it is appreciated that various other mechanisms for loading a container may be used.

Referring again to FIG. 5, the second web of material 430 conveyed along the path illustrated by arrow 435 may be from a printer and/or encoder which is configured to print or encode identifying information on the second web of material about the medication unit doses that are being dispensed to the corresponding container cavities 410. The printer (not shown) may print to the second web of material 430 using thermal printing, inkjet printing, dot matrix printing, or any other conventional printing method. Similarly, an encoder may be configured to encode radio frequency identification (RFID) tags embedded in or placed on the second web of material 430. The information written to the second web of material 430 may include identifying information about the medication being dispensed such as a medication name, a dosage, manufacturer information (e.g., name, location), manufacture date, expiration date, medication precautions, or any other information about the medication. The second web of material 430 may also be printed with a barcode that may identify the medication (e.g., by a national drug code number) or be encoded with information on an RFID tag which may be read by an RFID reader. The information encoded to a barcode or RFID tag may include more or less detail than the information presented in text. For example, an expiration date, medication source information, or other information may be encoded into the computer readable barcode or RFID tag.

As noted above, it is imperative that the unit dose medications that are dispensed to container cavities 410 be properly labeled. The identifying information printed (and/or encoded) on the second web of material 430 must correspond to the medication in the container cavities 410 such that medication is properly dispensed to patients, particularly when automation is used to store and dispense medication. Automation of medication distribution relies upon medication identification to be accurate in order to properly function. In some example embodiments the printed medication identification information may be configured to be no wider than 50% of the width of an individual container package, with duplicate information arranged immediately adjacent thereto. In this manner, the second web of material may be printed constantly throughout the dispensing of a medication, and precise alignment of the second web 430 to the individual container packages may not be necessary, as regardless of where one medication identification information may be cut between container packages, at least one full version of the medication identification information is assured to be present on each individual container package. In other example embodiments, each individual medication identification information that is printed may correspond to a container package. In such an embodiment, alignment of the medication identification information to each container package may be necessary.

In an example embodiment in which the medication identification information is to be aligned with a container package, indexing of both the container cavities 410 and the printed information 440 may be required. Such indexing may be performed, for example, by establishing the position of registration marks on the first web of material 405 and the second web of material 430. In one example embodiment, the image capture device (e.g., image capture device 230 of FIG. 2) may capture an image of indexing features of the formed containers and the printed identifying information such that the processor 200 may provide an offset to better align the printed information with the formed containers. As outlined further below, when a first web of material is joined to a second web of material, adjustment of their relative positions may be difficult such that offsets for the indexing of printing medication identification information may be implemented by the printer when determining the location for the information to be printed to the second web of material.

Upon dispensing a unit dose medication to a container cavity 410, the second web of material 430 including the proper medication identification information needs to be joined to the first web of material 405 that includes the container cavity 410. However, in order to verify that the medication identification information matches the medication dispensed to the container cavity, the automated packaging station 400 may perform a verification operation. The verification operation may include an image capture device 230 as illustrated in FIG. 5 configured to capture an image of the medication identification information 440. An image of the medication unit dose contained within the container cavity corresponding to the captured medication identification information may be captured substantially simultaneously. In the illustrated embodiment, a mirror 455 may be used such that a single image capture device 230 may simultaneously capture an image of the dispensed medication unit dose and the medication identification information that is to be joined to that container cavity. In another example embodiment, a separate image capture device may be used to capture an image of the medication unit dose. In another example embodiment, an image capture device may be used to capture an image of the dispensed unit dose medication while a scanner (e.g., a barcode scanner) or reader (e.g., an RFID reader) reads the identifying information from the printed label. The verification operation may be performed, for example, by processor 200 and may use character recognition software to read text of the medication identification information, and/or the barcode may be decoded to ascertain the medication type identified.

The image of the medication unit dose (captured, for example, by image capture device 230) may be transmitted to a processor (e.g., processor 200) or to a remote system for verification by communication interface 220. The image capture device 230 may communicate via the communications interface 220 with a processor or remote system via a wired or wireless connection, such as by a connection with a network (e.g., network 105 of FIG. 1). The captured image of the unit dose medication may be compared against a reference image of the medication identified by the medication identification information (which may be stored, for example, in memory device 215, or is otherwise accessible via a network 105), or against a plurality of identifying characteristics of the medication identified by the medication identification information in order to verify that the medication unit dose (both medication type and dose) matches the medication identification information. The plurality of identifying characteristics may include size, shape, color, indicia disposed on the medication unit dose, etc.

The comparison of the image of the unit dose of medication with the reference image or against the plurality of identifying characteristics may occur in a variety of ways. For example, a processor (e.g., processor 220) may analyze the captured image for a unit dose color, a unit dose shape, a unit dose size, indicia disposed on the unit dose, or any other identifying characteristics. These identifying characteristics may then be compared against the identifying characteristics of the medication identified in the medication identification information (e.g., stored in memory device 215) to determine if the medication unit dose and the medication identification information match. Upon determining a match, the unit dose medication may be verified as correct. Additionally or alternatively, the comparison of the image of the unit dose of medication may be against a reference image of the medication identified by the medication identification information. Upon determining that the medication unit dose matches the medication identified by the medication identification information, the medication may be positively verified.

While the above described mechanisms for verifying a unit dose of medication describe determining a "match" between the captured image and medication identified by the medication identification information, the "match" may be based on a confidence level. For example, as each captured image for each unit dose of medication may vary to some degree, exact matches for the captured image may not be established. Therefore, to improve the rate at which medications are properly verified, medication unit doses may be required to match the identified medication above a threshold level may be considered a "match."

In an example embodiment of establishing a match, a captured image of a unit dose of medication, captured by image capture device 230 and sent to processor 200, may include where the identified medication matches the color, shape, and size of the medication unit dose in the captured image, but the indicia on the medication in the captured image is only a partial match to the indicia of the medication identified, the match may be established. Since indicia may be difficult to read or may be obscured during the manufacturing process, a clear identification of the indicia may not be possible. As such, matching all other attributes and partially matching the indicia of the medication may satisfy the threshold above which it is determined that the medication of the image matches the identified medication.

The threshold confidence level which must be satisfied to establish a match between a unit dose of medication in a captured image and the identified medication may be variable and may be calibrated in order to achieve a minimum accuracy rate (e.g., 99.9999%). The threshold may also vary depending upon the characteristics of the medication. For example, many medications are small, white pills. As such, when a white pill is the unit dose of medication in the captured image, the confidence threshold that must be satisfied may be substantially higher than if the unit dose of medication in the captured image is a pink and purple capsule, where a database of known medications includes only one medication unit dose with a pink and purple capsule.

The threshold confidence level may be a weighted formula based upon the various features compared between the captured image and the identified medication. For example, the color of a medication may be allowed to vary up to 5% on an established scale, whereas the shape of a unit dose of medication may only be allowed to vary 2% from an established shape.

Upon successful verification of the unit dose of medication (e.g., upon the processor 200 establishing that the unit dose medication of the captured image satisfies the confidence threshold for matching the identified medication), the unit dose of medication is considered positively verified.

Once the medication unit dose is verified to be the medication identified by the medication identification information, the first web of material 405 is joined to the second web of material 430. The webs may be joined, for example, by ultrasonic welding or by heat sealing (e.g., lamination). FIG. 5 illustrates a mechanism 470 by which the webs are joined through heat sealing. As shown, the first web of material 405 and the second web of material 430 are conveyed along separate paths between guide rollers 480 during the dispensing and verification operations. After the dispensing and verification, the webs are joined at 470.

While the above examples illustrate example embodiments in which the unit dose of medication is positively verified, embodiments of the invention further provide for mismatches between the medication unit dose and the medication identified by the medication identification information, such as in an embodiment in which the confidence threshold of the medication is not satisfied. For example, if a captured image of a unit dose of medication is too dark, too blurred, or if the physical appearance of the medication does not closely match the medication identified, the confidence threshold may not be satisfied. Upon failing to satisfy the confidence threshold for a particular unit dose of medication, the operator may be alerted to the issue. In some embodiments, the automated packaging station 400 may cease operation until the issue is addressed and an operator confirms that packaging should continue (e.g., through user interface 205). In another example embodiment, the packaged medication unit doses may be separated from one another (e.g., by a container singulator) and the erroneous medication unit dose may be redirected to a location where the improperly labeled medication unit dose may be disposed of or repackaged.

In an example embodiment, a printer may be located downstream of the verification operation and may be configured to over-print a label to the second web of material for erroneously labeled medication unit doses in order to alert an operator and preclude dispensing of the over-printed label. The over-printing may be a mark of a differing color (e.g., a red cross out), or may be any such mark to indicate that the medication was improperly packaged. Such a printer may receive information regarding an erroneous container from processor 200 via communications interface 220.

Referring back to FIG. 5, in an embodiment in which a medication unit dose hopper is used for automated dispensing of unit doses to container cavities, the unit dose hopper 420 may include medication identifying information 422 thereon. The medication identifying information 422 of the hopper 420 may be configured to be within the field of view of the image capture device 230, or optionally, a separate image capture device or scanner (barcode or RFID) may be configured to view or read the medication identifying information 422 of the hopper 420. In this manner, the verification operation may include verifying that the medication identification information of the hopper 420 matches that of the second web 430 and both match the medication unit dose dispensed to the container cavity. In the event the incorrect hopper 420 is arranged to dispense medication unit doses, an alert may be generated in order for an operator to correct the error. Additionally or alternatively, a pharmacist may verify the medication in the hopper is correct prior to dispensing medication from the hopper.

According to example embodiments of the present invention, medications may be dispensed to and packaged in unit dose container packaging in an efficient manner. In particular, the medications that are being packaged can readily be changed by an operator to switch between medication types being packaged. For example, if there is a need for one hundred unit doses of a first type of medication, fifty unit doses of a second type of medication, and seventy unit doses of a third type of medication, the automated packaging station 400 may print one hundred medication identification information labels for the first medication as the unit doses are dispensed. Upon reaching one hundred unit doses printed, the printing may switch to the second type of medication to be dispensed, even if the first medication is still being physically dispensed. This may occur when the printing station is upstream of the dispensing station by one or more unit dose labels. After one hundred unit doses of the first medication type have been dispensed, the operator may be prompted (via user interface 205) to switch the hopper 420 to the second type of medication or to manually dispense the second type of medication. Packaging may then continue until each of the second type of medication unit doses have been dispensed and packaged. In this manner, sequential packaging of medications may occur without sacrificing excess material webbing between medication types. Further, visual verification of the medication combined with scanning of the medication identification information of the label may permit fewer manual verification steps increasing the efficiency of operators and pharmacists.

According to some example embodiments of the present invention, when a plurality of different types of medications need to be packaged at the automated packaging station, the controller 125 may be configured to receive an indication of each of the medication types and their quantities. The controller may also be configured to organize the order in which the medication types are to be packaged. In a further effort to reduce the likelihood of medication confusion or mislabeling, the controller 125 may be configured to determine the physical appearance of each of the medication unit doses that are to be packaged (e.g., obtaining reference images or identifying characteristics from memory device 215). If two medication unit doses are very similar in appearance such that there is a higher likelihood of confusion, the controller 125 may be configured to not process those two medications through the automated packaging station in direct sequence (consecutively) with one another. Said differently, at least one other medication of dissimilar appearance may be packaged between the packaging of the medication unit doses with similar appearances. Not packaging medication unit doses with similar appearances consecutively may reduce the likelihood of mislabeling or erroneous identification of a medication.

The similarity of appearance of medications may be determined based on the identifying characteristics of the medications. For example, medications with the same size, shape, and color, but with different indicia embossed thereon may be considered similar in appearance. The similarities may be established in the same manner as outlined above with respect to identifying medications. Thresholds may be established in which medications that are above a predefined threshold of similarity of appearance with one another may not be processed consecutively. Processing medications of similar appearance consecutively, when it is not possible to avoid such a scenario, may require additional verification steps when changing from packaging the first medication to packaging the second medication. Further, the thresholds for verification of the correct medication may be elevated in response to two medications of similar appearance being processed in sequence. For example, if two medications are to be processed in sequence and the processor 200 establishes that the only discernible difference in their appearance is the shape of the unit dose, the threshold for verification of a unit dose based upon the shape may be elevated in order to further minimize the likelihood of improperly packaging the medications.

FIG. 7 illustrates an example embodiment of a method for verifying unit doses of medication during a packaging operation. An indication of medication information is received at operation 600. The indication of medication information may be, for example, an order for a number of unit doses of a medication to restock a supply of the medication including medication information. The order for a number of unit doses may be generated by, for example, an automated storage/dispensing system when the system detects the remaining quantity of a medication to be below a threshold value. Identifying information related to the medication information may be printed to a web of material at 610. Identifying information may include the medication name, dosage, manufacturer information, etc., which is related to the medication information received at operation 600. A medication unit dose is dispensed at 620 to a container. At 630, a verification process is performed to verify that the unit dose dispensed to the container corresponds to the identifying information printed to the web of material. The web of material that is the lidding material is joined to the container in response to the unit dose corresponding to the identifying information.

In an example embodiment, an apparatus for performing the method of FIG. 7 above may include a processor (e.g., the processor 200) configured to perform some or each of the operations (600-640) described above. The processor 200 may, for example, be configured to perform the operations (600-640) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 600-640 may comprise, for example, the packaging station controller 125 (or respective different components thereof). Additionally or alternatively, at least by virtue of the fact that the processor 200 may be configured to control or even be embodied as the packaging station controller 125, the processor 200 and/or a device or circuitry for executing instructions or executing an algorithm for processing information as described above may also form example means for performing operations 600-640.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe some example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:
1. An apparatus configured to package unit dose medications into containers comprising:
   a printer configured to print identifying information about a medication to a web of material;
   a dispenser configured to dispense a plurality of medication unit doses of different medication types, each to a respective container;
   an image capture device configured to capture an image of at least one of the printed web or a dispensed medication unit dose;
   a processor configured to verify that a dispensed medication unit dose matches identifying information of the printed web; and
   a joining station configured to join the printed web to a container containing the dispensed medication unit dose in response to the processor verifying that the dispensed medication unit dose matches the identifying information of the printed web;
   wherein the processor is configured to determine an order of dispensing of a plurality of different types of medications, and wherein the processor is configured to separate, within the order of dispensing, medications having a similar appearance by at least one medication there between having a dissimilar appearance in the order of dispensing of the plurality of different types of medications, wherein medications of similar appearance have a combination of color, shape, size, and indicia that satisfies a similarity threshold, and wherein medications of dissimilar appearance have a combination of color, shape, size, and indicia that does not satisfy the similarity threshold.

2. The apparatus of claim 1, wherein identifying information about a medication comprises medication type and medication dose.

3. The apparatus of claim 1, wherein the joining station comprises at least one of an ultrasonic welder or a heating element, each configured to seal the printed web of material to the container containing the dispensed medication unit dose.

4. The apparatus of claim 1, further comprising an indexing station configured to align the printed identifying information with the container containing the dispensed medication unit dose.

5. The apparatus of claim 1, further comprising a medication hopper configured to supply medication to the dispenser.

6. The apparatus of claim 1, further comprising a container forming station configured to form containers from a second web of material.

7. The apparatus of claim 1, wherein the image capture device is configured to capture an image of the printed web and the dispensed medication unit dose simultaneously.

8. The apparatus of claim 7, wherein the processor compares the identifying information about a medication on the web of material to the dispensed medication.

9. The apparatus of claim 8, wherein the processor generates an alert in response to the identifying information about the medication on the web of material failing to correspond with the dispensed medication.

10. The apparatus of claim 1, wherein the unit dose container and the printed web of material are aligned with each other based on registration marks on the printed web of material and a web of material from which the unit dose container is formed.

11. The apparatus of claim 1, wherein the image capture device is further configured to verify the dispensed medication unit dose as a correct medication type.

12. The apparatus of claim 11, wherein in response to an order of dispensing of a plurality of different types of medication including two medication types that are dissimilar in appearance by one or more of shape, color, size, or indicia, increasing a threshold for verification of a unit dose of medication relative to the one or more of shape, color, size, or indicia.

\* \* \* \* \*